United States Patent [19]

Weider et al.

[11] Patent Number: 5,684,214

[45] Date of Patent: Nov. 4, 1997

[54] PROCESS FOR PREPARING 1,3-PROPANEDIOL

[75] Inventors: Paul Richard Weider; Joseph Broun Powell; Khiet Thanh Lam, all of Houston, Tex.

[73] Assignee: Shell Oil Company, Houston, Tex.

[21] Appl. No.: 550,589

[22] Filed: Oct. 31, 1995

Related U.S. Application Data

[63] Continuation-in-part of Ser. No. 316,676, Sep. 30, 1994, abandoned.

[51] Int. Cl.$^6$ .................................................. C07C 27/04
[52] U.S. Cl. ............................................ 568/862; 568/483
[58] Field of Search ................................ 568/862, 483

[56] References Cited

U.S. PATENT DOCUMENTS

| | | | |
|---|---|---|---|
| 3,687,981 | 8/1972 | Laurence et al. | 260/340.7 |
| 5,030,766 | 7/1991 | Priggs et al. | 568/496 |

FOREIGN PATENT DOCUMENTS 56114834  9/1981  Japan .

OTHER PUBLICATIONS

Falbe, Carbon Monoxide in Organic Synthesis, Springer–Verlag (1970) pp. 1, 14–15.
Falbe, New Syntheses with Carbon Monoxide, Springer–Verlag (1980), p. 1, 131.
Fachinetti et al., "CO$_2$(CO)$_8$–promoted dihydrogen activations under unusually mold conditions by highly polarizing CO$^{2+}$cations", *J. Organomet. Chem.*, 353 (1988) 393–404.
Kemmitt and Russel, "Comprehensive Organometallic Chemistry," vol. 5, p. 5 1980.

*Primary Examiner*—Rebecca Cook

[57] ABSTRACT

A process for preparing 1,3-propanediol comprises the steps of:

(a) reacting a cobalt salt selected from at least one of cobalt hydroxide, cobalt (II, III) oxide and cobalt carbonate with synthesis gas in an essentially non-water-miscible liquid medium under conditions effective to produce a cobalt carbonyl reaction product comprising at least one active cobalt carbonyl hydroformylation catalyst species;

(b) contacting ethylene oxide with synthesis gas in an essentially non-water miscible liquid medium in the presence of a catalytic amount of the cobalt carbonyl reaction product mixture and an effective amount of a catalyst promoter under reaction conditions effective to produce an intermediate product mixture comprising less than 15 wt % 3-hydroxypropanal;

(c) adding an aqueous liquid to said intermediate product mixture and extracting into said aqueous liquid a major portion of the 3-hydroxypropanal so as to provide an aqueous phase comprising 3-hydroxypropanal in greater concentration than the concentration of 3-hydroxypropanal in the intermediate product mixture, and an organic phase comprising a major portion of the cobalt carbonyl;

(d) separating the aqueous phase from the organic phase;

(e) returning at least a major portion of the organic phase to the process of step (b);

(f) contacting the aqueous phase comprising 3-hydroxypropanal with hydrogen in the presence of a hydrogenation catalyst under hydrogenation conditions to provide a hydrogenation product mixture comprising 1,3-propanediol; and (g) recovering 1,3-propanediol from the hydrogenation product mixture.

13 Claims, 1 Drawing Sheet

PROCESS FOR PREPARING 1,3-PROPANEDIOL

REFERENCE TO RELATED APPLICATION

This application is a continuation-in-part of Ser. No. 316,676, filed Sep. 31, 1994, abandoned.

BACKGROUND OF THE INVENTION

This invention relates to the preparation of 1,3-propanediol. In one aspect, the invention relates to a cobalt-catalyzed process for manufacturing 1,3-propanediol. In a specific aspect, the invention relates to the preparation of a recyclable cobalt catalyst in a cobalt-catalyzed process for manufacturing 1,3-propanediol.

1,3-propanediol (PDO) is an intermediate in the production of polyesters for fibers and films. It is known that PDO can be prepared in a two-step process involving (1) the cobalt-catalyzed hydroformylation (reaction with synthesis gas, $H_2/CO$) of ethylene oxide to intermediate 3-hydroxypropanal (HPA), and (2) hydrogenation of the HPA to PDO. An improved synthesis process has been developed permitting the hydroformylation step to be carried out selectively at relatively low temperature and pressure. For the process to be economical, it is necessary that essentially all the cobalt hydroformylation catalyst be simply recovered and recycled to the hydroformylation reactor.

The active cobalt catalyst for the hydroformylation step is a cobalt carbonyl compound. For reasons of process economics, the cobalt carbonyl catalyst is typically prepared from cobalt (II) salts such as cobalt octoate or cobalt acetate. Such salts are generally converted to cobalt carbonyls by reduction of the carboxylic acid salts of cobalt at elevated temperature and pressure. Concurrent with the production of the desired cobalt carbonyls, however, free organic acid is also generated. The inventors have found that, in the hydroformylation of ethylene oxide in the improved PDO preparation process, these carboxylic acids act to alter the nature of the catalyst and complicate cobalt recovery and recycle. It would be desirable to generate cobalt carbonyls in the PDO preparation process without generating side reactions which can interfere with catalyst recovery and recycle.

It is therefore an object of the invention to provide a PDO preparation process in which a recyclable cobalt carbonyl hydroformylation catalyst is prepared without generating by-products which interfere with catalyst recovery and/or recycle.

BRIEF SUMMARY OF THE INVENTION

According to the invention, a process for preparing 1,3-propanediol is provided comprising the steps of:

(a) reacting a cobalt precursor compound selected from at least one of cobalt hydroxide, cobalt (II, III) oxide and cobalt carbonate with synthesis gas in an essentially non-water-miscible liquid medium under conditions effective to produce a cobalt carbonyl reaction product mixture comprising at least one active cobalt carbonyl hydroformylation catalyst species;

(b) contacting ethylene oxide with carbon monoxide and hydrogen in an essentially non-water miscible solvent in the presence of a catalytic amount of the cobalt carbonyl reaction product mixture and an effective amount of a catalyst promoter under reaction conditions effective to produce an intermediate product mixture comprising less than 15 wt % 3-hydroxypropanal;

(c) adding an aqueous liquid to said intermediate product mixture and extracting into said aqueous liquid a major portion of the 3-hydroxypropanal so as to provide an aqueous phase comprising 3-hydroxypropanal in greater concentration than the concentration of 3-hydroxypropanal in the intermediate product mixture, and an organic phase comprising a major portion of the at least one cobalt carbonyl;

(d) separating the aqueous phase from the organic phase;

(e) returning at least a major portion of the organic phase to the process of step (b);

(f) contacting the aqueous phase comprising 3-hydroxypropanal with hydrogen in the presence of a hydrogenation catalyst under hydrogenation conditions to provide a hydrogenation product mixture comprising 1,3-propanediol; and (g) recovering 1,3-propanediol from the hydrogenation product mixture.

The invention enables the preparation of PDO in a process in which active cobalt carbonyl species for the hydroformylation step are generated without the creation of by-products which interfere with efficient recovery and recycle of the catalyst.

DETAILED DESCRIPTION OF THE INVENTION

Figure 1:
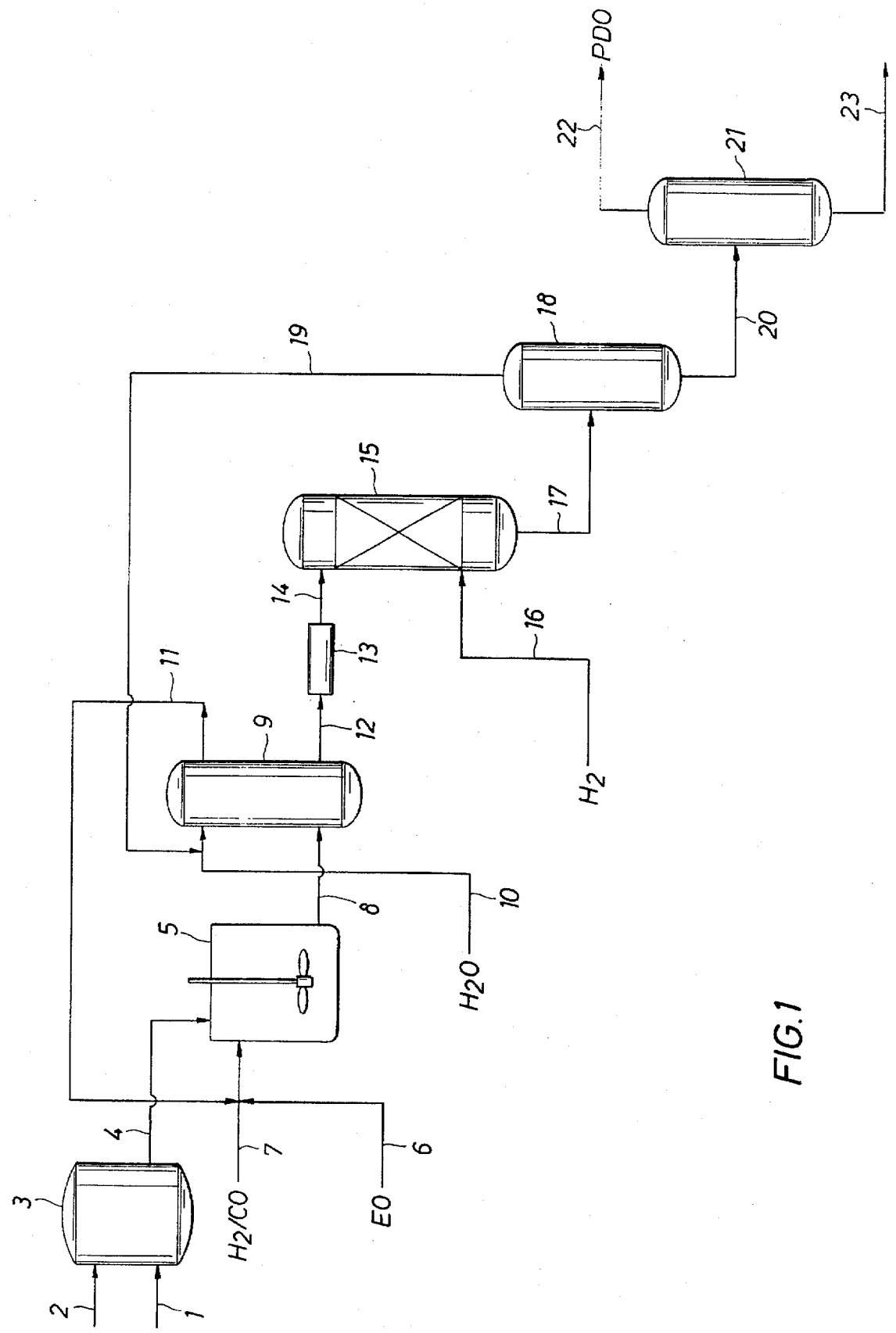
FIG. 1 is a schematic flow diagram of one embodiment of the invention 1,3-propanediol preparation process.

The invention 1,3-propanediol preparation process can be conveniently described by reference to FIG. 1. Separate or combined streams of carbon monoxide and hydrogen 1 and the cobalt carbonyl precursor 2 selected from cobalt hydroxide, cobalt oxide and cobalt carbonate are charged to mixing vessel 3 and are contacted under reducing conditions in a liquid medium. The medium selected for the cobalt carbonyl preparation is preferably, for greatest economy of the overall process, the same as that chosen for the hydroformylation step, as described in detail below. The currently preferred medium is methyl-t-butyl ether. The precursor cobalt compound can be cobalt hydroxide, cobalt oxide or cobalt carbonate. Of these, cobalt hydroxide is preferred because of its fast rate and water by-product.

The catalyst preparation step is carried out at elevated temperature, suitably at a temperature within the range of about 60° to about 160° C., preferably within the range of about 80° to about 120° C., and at elevated pressure, suitably within the range of about 400 to about 2500 psig, preferably about 1000 to about 1600 psig. The synthesis gas is present at a ratio of $H_2:CO$ within the range of about 1:2 to about 8:1, preferably about 1:1 to about 5:1. Under these conditions, the conversion to the desired cobalt carbonyl species occurs very rapidly and holding time of less than about 60 minutes will generally be required.

It is preferred to initiate the catalyst preparation step in the presence of a minor amount of a "seed" compound. Suitable seed compounds include compounds of noble metals such as platinum and palladium and amines such as nonylpyridine. The preferred seed compound is cobalt octacarbonyl. The seed cobalt carbonyl is present in an amount sufficient to promote the conversion of $Co^{+2}$ to $Co^0$ and to assist in the dissolution of the cobalt precursor in the liquid medium, generally an amount of at least about 0.4 mole percent, based on total moles of cobalt. The seed compound is used only in start-up of the reaction, which is "self-seeding" once initiated. Initiation of catalyst preparation can be carried out by adding the catalyst precursor and the seed compound at room temperature to the reaction slurry prior to introduction of syngas to the reactor. Once the reaction has been initiated, the catalyst precursor can be injected directly into the reaction mixture, preferably as a concentrated solution, under catalyst preparation conditions. The product of the catalyst preparation step includes at least one of dicobaltoctacarbonyl and cobalt hydridocarbonyl, generally a mixture of these cobalt carbonyls.

It is optional but preferable, for increased reaction rate, for the catalyst preparation reaction mixture to include a minor amount of water. An optimum amount of water will be achieved by adding sufficient water to the liquid medium to bring the water level therein to about 0.5 to about 3 wt %, based on the weight of the liquid medium. Excess water should be avoided to prevent formation of a separate water phase as the reaction proceeds.

The catalyst reaction mixture containing active cobalt carbonyl catalyst species is passed via 4 to hydroformylation vessel 5. Although FIG. 1 illustrates an embodiment in which cobalt carbonyl preparation takes place in a separate reaction vessel the products of which feed into the hydroformylation vessel, it is also possible to prepare the active cobalt carbonyl species in the hydroformylation vessel, ideally by adding the precursor cobalt compound directly to the hydroformylation vessel and preparing the cobalt carbonyl species in situ.

In hydroformylation vessel 5, the active catalyst is mixed with ethylene oxide 6 and synthesis gas 7 in a non-water-miscible liquid medium. The hydroformylation vessel is a suitable pressure reaction vessel such as a bubble column and/or agitated tank, operated batchwise or continuously. The hydrogen and carbon monoxide will generally be introduced into the reaction vessel in a molar ratio within the range of about 1:2 to about 8:1, preferably about 1.5:1 to about 5:1. The amount of cobalt present in the hydroformylation reaction mixture will vary depending upon the other reaction conditions, but will generally fall within the range of about 0.01 to about 1 wt %, preferably about 0.05 to about 0.3 wt %, based on the weight of the reaction mixture.

The reaction is carried out under conditions effective to produce a hydroformylation reaction product mixture containing a major portion of 3-hydroxypropanal (HPA) and a minor portion of acetaldehyde, while maintaining the level of 3-hydroxypropanal in the reaction mixture at less than 15 wt %, preferably within the range of about 5 to about 10 wt %. (To provide for solvents having different densities, the desired concentration of HPA in the reaction mixture can be expressed in molarity, i.e., less than 1.5M, preferably within the range of about 0.5 to about 1M.)

Generally, the hydroformylation reaction is carried out at elevated temperature less than 100° C., preferably about 60° to about 90° C., most preferably about 75° to about 85° C., and at a pressure within the range of about 500 to about 5000 psig, preferably (for process economics) about 1000 to about 3500 psig, with higher pressures within this range preferred for greater selectivity. The concentration of 3-hydroxypropanal in the intermediate product mixture can be controlled by regulation of process conditions such as ethylene oxide concentration, catalyst concentration, reaction temperature and residence time. In general, relatively low reaction temperatures (below about 90° C.) and relatively short residence times (about 20 minutes to about 1 hour) are preferred. In the practice of the invention method, it is possible to achieve HPA yields (based on ethylene oxide conversion) of greater than 80%, with formation of greater than 7 wt % HPA, at rates greater than 30 h$^{-1}$. (Catalytic rates are referred to herein in terms of "turnover frequency" or "TOF" and are expressed in units of moles per mole of cobalt per hour, or h$^{-1}$.).

The hydroformylation reaction is carried out in a liquid solvent inert to the reactants. By "inert" is meant that the solvent is not consumed during the course of the reaction. In general, ideal solvents for the process will solubilize carbon monoxide, will be essentially non-water-miscible and will exhibit low to moderate polarity such that the 3-hydroxypropanal intermediate will be solubilized to the desired concentration of at least about 5 wt % under hydroformylation conditions, while significant solvent will remain as a separate phase upon water extraction. By "essentially non-water-miscible" is meant that the solvent has a solubility in water at 25° C. of less than 25 wt %, so as to form a separate hydrocarbon-rich phase upon water extraction of HPA from the hydroformylation reaction mixture. Preferably this solubility is less than about 10%, most preferably less than about 5 wt %. The solubilization of carbon monoxide in the selected solvent will generally be greater than 0.15 v/v (1 atm, 25° C.), preferably greater than 0.25 v/v, as expressed in terms of Ostwald coefficients.

The preferred class of solvents are alcohols and ethers which can be described according to the formula

in which $R^1$ is hydrogen or $C_{1-20}$ linear, branched, cyclic or aromatic hydrocarbyl or mono- or polyalkylene oxide and $R_2$ is $C_{1-20}$ linear, branched, cyclic or aromatic hydrocarbyl, alkoxy or mono- or polyalkylene oxide. The most preferred hydroformylation solvents can be described by the formula

in which $R_1$ is hydrogen or $C_{1-8}$ hydrocarbyl and $R_3$, $R_4$ and $R_5$ are independently selected from $C_{1-8}$ hydrocarbyl, alkoxy and alkylene oxide. Such ethers include, for example, methyl-t-butyl ether, ethyl-t-butyl ether, diethyl ether, phenylisobutyl ether, ethoxyethyl ether, diphenyl ether and diisopropyl ether. Blends of solvents such a tetrahydrofuran/toluene, tetrahydrofuran/heptane and t-butylalcohol/hexane can also be used to achieve the desired solvent properties. The currently preferred solvent, because of the high yields of HPA which can be achieved under moderate reaction conditions, is methyl-t-butyl ether.

The hydroformylation reaction mixture will preferably include a catalyst promoter to accelerate the reaction rate. Suitable promoters include sources of mono- and multivalent metal cations of weak bases such as alkali, alkaline earth and rare earth metal salts of carboxylic acids. Also suitable and preferred are lipophilic promoters such as lipophilic phosphonium salts and lipophilic amines, which accelerate the rate of hydroformylation without imparting hydrophilicity (water solubility) to the active catalyst. As used herein, "lipophilic" means that the promoter tends to remain in the organic phase after extraction of HPA with water. The promoter will generally be present in an amount within the range of about 0.01 to about 0.6 moles per mole of cobalt. Suitable metal salts include sodium, potassium and cesium acetates, propionates and octoates; calcium carbonate and lanthanum acetate. The currently preferred hydroformylation catalyst promoter is tetrabutylphosphonium acetate.

It is generally preferred to regulate the concentration of water in the hydroformylation reaction mixture, as excessive amounts of water reduce (HPA+PDO) selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally being more tolerant of higher water concentrations. For example, optimum water levels for hydroformylation in methyl-t-butylether solvent are believed to be within the range of about 1 to about 2.5 wt %.

Following the hydroformylation reaction, hydroformylation reaction product mixture 8 containing 3-hydroxypropanal, the reaction solvent, 1,3-propanediol, the cobalt catalyst and a minor amount of reaction by-products, is cooled and passed to extraction vessel 9, wherein an aqueous liquid, generally water and optional miscibilizing solvent, are added via 10 for extraction and concentration of the HPA for the subsequent hydrogenation step. Liquid extraction can be effected by any suitable means, such as mixer-settlers, packed or trayed extraction columns, or rotating disk contactors. Extraction can, if desired, be carried out in multiple stages. The water-containing hydroformylation reaction product mixture can optionally be passed to a settling tank (not shown) for resolution of the mixture into aqueous and organic phases. The amount of water added to the hydroformylation reaction product mixture will generally be such as to provide a water:mixture ratio within the range of about 1:1 to about 1:20, preferably about 1:5 to about 1:15. The addition of water at this stage of the reaction may have the additional advantage of suppressing formation of undesirable heavy ends. Extraction with a relatively small amount of water provides an aqueous phase which is greater than 20 wt % HPA, preferably greater than 35 wt % HPA, permitting economical hydrogenation of the HPA to PDO and recovery of PDO product. The water extraction is preferably carried out at a temperature within the range of about 25° to about 55° C., with higher temperatures avoided to minimize condensation products (heavy ends) and catalyst disproportionation to inactive, water-soluble cobalt species. In order to maximize catalyst recovery, it is optional but preferred to perform the water extraction under 50 to 200 psig carbon monoxide at 25° to 55° C.

The organic phase containing the reaction solvent and the major portion of the cobalt catalyst can be recycled from the extraction vessel to the hydroformylation reaction via 11. Aqueous extract 12 is optionally passed through one or more acid ion exchange resin beds 13 for removal of any cobalt catalyst present, and the decobaited aqueous product mixture 14 is passed to hydrogenation vessel 15 and reacted with hydrogen 16 in the presence of a hydrogenation catalyst to produce a hydrogenation product mixture 17 containing 1,3-propanediol. The hydrogenation step may also revert some heavy ends to PDO. The solvent and extractant water 19 can be recovered by distillation in column 18 and recycled to the water extraction process via a further distillation (not shown) for separation and purge of light ends. PDO-containing stream product 20 can be passed to distillation column 21 for recovery of PDO 22 from heavy ends 23.

Hydrogenation of the HPA to PDO can be carried out in aqueous solution at an elevated temperature during at least a portion of the hydrogenation step of about 40° C., generally within the range of about 50° to about 175° C., under a hydrogen pressure of at least about 100 psig, generally within the range of about 200 to about 2000 psig. The reaction is carried out in the presence of a hydrogenation catalyst such as any of those based upon Group VIII metals, including nickel, cobalt, ruthenium, platinum and palladium, as well as copper, zinc and chromium and mixtures and alloys thereof. Nickel catalyst, including bulk, supported and fixed-bed forms, provide acceptable activities and selectivities at moderate cost. Highest yields are achieved under slightly acidic reaction conditions.

Commercial operation will require efficient cobalt catalyst recovery with essentially complete recycle of cobalt to the hydroformylation reaction. The preferred catalyst recovery process involves two steps, beginning with the above-described water extraction of HPA from the hydroformylation product mixture. A portion of the cobalt catalyst may remain in the organic phase, with the remaining cobalt catalyst passing into the water phase. The organic phase can be recycled to the hydroformylation reactor, with optional purge of heavy ends. Optionally, further decobaiting of catalyst in the water layer can be effected by any suitable method, such as complete or partial oxidation of cobalt followed by precipitation and filtration, distillation, deposition on a solid support, or extraction using a suitable extractant, preferably prior to final cobalt removal by ion exchange (13).

The invention process permits the selective and economic synthesis of PDO at moderate temperature and pressures with essentially complete recycle of the cobalt carbonyl hydroformylation catalyst.

EXAMPLE 1

Preparation of Cobalt Carbonyl from Cobalt Hydroxide in Anhydrous MTBE

Into a 30 ml stainless steel autoclave fitted with internal infrared optics was added 404 mg (4.3 millimole) of cobaltous hydroxide and 17 ml of anhydrous MTBE. The reactor was sealed, purged with nitrogen and placed under 1200 psi of 2:1 synthesis gas (H2:CO). The sealed reactor was heated to 140° C. over the course of several minutes and the internal pressure was allowed to rise to 1470 psi. No conversion of cobaltous hydroxide was noted within 320 minutes. No formation of cobalt carbonyls was observed in the infrared spectrum between 2100 to 1960 cm$^{-1}$. No syn gas consumption was noted. After 320 minutes of stirring at 140° C., the reaction mixture was cooled and the mixture was removed. A clear, colorless supernatant with a bright pink suspended solid supported the conclusion that no preforming had taken place in the absence of both water and seed compound.

EXAMPLE 2

Preparation of Cobalt Carbonyl from Cobalt Hydroxide in Aqueous MTBE

This experiment illustrates the promotional effect of water on the invention catalyst separation process. Into a 30 ml stainless steel autoclave fitted with internal infrared optics was added 210 mg (2.16 millimoles) of cobaltous hydroxide and 35 mg (0.102 millimoles) of dicobalt octacarbonyl seed. To this was added 17 ml of MTBE containing 1% water. The reactor was sealed, purged with nitrogen and placed under 980 psi of 1:1 synthesis gas (H2:CO). The sealed reactor was heated to 120° C. over the course of several minutes and the internal pressure was allowed to rise. The progress of the conversion of cobaltous hydroxide was monitored quantitatively by changes in the infrared spectrum. The concentration of cobaltous hydroxide was tracked by the O—H stretching frequency at 3630 cm$^{-1}$, and the formation of cobalt carbonyl was monitored by the growth of the metal carbonyl bonds in the region from 2100 to 1960 cm$^{-1}$.

Analysis of the infrared spectra indicated a dissolution of cobaltous hydroxide followed by a rapid conversion of cobaltous hydroxide to cobalt carbonyls. The formation of cobalt carbonyls was accompanied by a rapid consumption of syngas. Complete conversion (>98%, as measured by absorbance intensities of the metal carbonyl region) was observed within 35 minutes of reaching 120° C. The patterns observed in the metal carbonyl region indicated that the solution was an equilibrium mixture of $Co_4(CO)_{12}$, $Co_2(CO)_8$ and $HCo(CO)_4$, with a small amount of $[Co(CO)_4]^-$. When the reaction mixture was cooled and the liquid removed, a homogeneous, dark coffee-brown solution characteristic of cobalt carbonyl mixtures was obtained. No precipitates of any kind were observed.

EXAMPLE 3

Comparison Preforming Experiment with Cobalt Acetate 15.8 g of cobalt acetate tetrahydrate, 3.72 g nonylpyridine promoter and 18.75 g toluene marker in 1873 g methyl-t-butyl ether were heated to 120° C. under 1400 psi 2:1 $H_2/CO$ in a one-gallon stirred reactor to preform cobalt carbonyl catalyst. Preforming was complete in 2.5 hours, as evidenced by lack of solids in samples removed from the reactor.

The reactor was cooled to 80° C. and 115 g ethylene oxide were injected. After 40 minutes, 4.8 wt % of the desired 3-hydroxypropanal (HPA) intermediate was observed. The reactor was cooled to 25° C. and of 175 g deionized water were introduced for extraction of product. 214.6 g of an aqueous layer containing 24 wt % HPA and 1892 ppm cobalt were isolated. The remaining 1900.6 g of organic solvent contained 2250 ppm cobalt. Thus, 91% of the cobalt catalyst remained with the organic solvent layer and was available for recycle to the reaction.

After removal of water, the reaction/extraction sequence was twice repeated by reheating the reaction mixture to 80° C., adding 110–125 g ethylene oxide, reacting for about 1 hour, cooling and extracting with 175 g deionized water. The aqueous layers contained 1463 and 893 ppm cobalt for the second and third runs, respectively, corresponding to recycle of 88 and 93% of the remaining cobalt with the upper solvent layer.

The entire experiment was repeated with a fresh charge of materials, with 25.3 g of deionized water used for extraction. The aqueous product contained 3300 ppmw cobalt, compared with 1892 ppm observed in the initial run above. Only 80% of the cobalt present was recycled with the organic solvent layer.

EXAMPLE 4

Cobalt Preforming with Dicobalt Octacarbonyl

The preforming experiment of Example 3 was twice repeated with 25 g of deionized water added to the reaction mixture (to simulate recycle conditions) using 10.875 g of dicobaltoctacarbonyl instead of cobalt acetate. Only 610 and 328 ppm cobalt appeared in the aqueous product for the two runs, respectively, representing cobalt recycles of 96 and 98% with the organic layer. Cobalt recycle in the organic solvent was thus improved in the absence of acetic acid by-product of catalyst preforming from cobalt acetate.

EXAMPLE 6

Cobalt Preforming with Cobalt 2-Ethylhexanoate (Cobalt Octoate)

A hydroformylation reaction was conducted in a 300 ml stirred reactor with addition of 0.87 g dicobaltoctacarbonyl, 0.30 g nonylpyridine, 1.5 g toluene marker, 2.0 g deionized water, 143 g methyl t-butyl ether and 4.5 g 2-ethylhexanoic acid. The latter amount was calculated as the steady-state concentration of organic acid expected to accumulate in a process using cobalt 2-ethylhexanoate as the salt used to make up cobalt losses, with water extraction to recover 3-HPA product. Separate studies of equilibrium partitioning between organic and aqueous solutions were conducted for this assessment.

13 g of ethylene oxide were charged under 1400 psi of 2:1 $H_2/CO$ and were hydroformylated for 70 minutes. After cooling to room temperature, the reaction mixture was extracted with 34 g of deionized water, yielding 38 g of an aqueous layer containing 2004 ppm cobalt and 116.8 g of an upper organic layer containing 621 ppm cobalt. Only 49% of the cobalt remained with the organic layer following water extraction.

This experiment shows that, at octanoic acid concentrations representative of calculated steady-state operation, significant cobalt would be lost upon aqueous extraction if a "cobalt octoate" (2-ethyl hexanoate) precursor were used to supply makeup cobalt to the system.

EXAMPLE 6

Cobalt Preforming with Cobalt Hydroxide

Example 5 was repeated with addition of 0.40 g cobalt hydroxide and no added acid. (Upon preforming, cobalt hydroxide releases water as a byproduct in minute amounts relative to the 2 weight percent water present in the methyl t-butyl ether solvent recycled from the water extraction step.) The cobalt hydroxide solution was preformed without a promoter but was initiated with 0.10 g of dicobaltoctacarbonyl. Infrared spectra taken after 8 hours of preforming at 140° C. under 2:1 $H_2/CO$ at 1400 psi indicated complete preforming of cobalt hydroxide to cobalt carbonyls.

The temperature was reduced to 80° C., and 0.52 g of tetra-n-butylphosphonium acetate was added to promote the hydroformylation reaction, producing acetic acid concentrations an order of magnitude less than those obtained in Example 3. Extraction was effected by addition of 33.3 g of water at room temperature. 35.8 g of aqueous product containing 185 ppm cobalt were isolated. 97% of the cobalt catalyst was recycled with the upper solvent layer following solvent extraction.

EXAMPLE 7

Cobalt Preforming with Cobalt Oxide

This experiment illustrates preforming of cobalt catalyst from cobalt oxide in the presence of water and catalyst seed.

Into a 30-ml stainless steel autoclave fitted with internal infrared optics was added 332 milligrams (1.38 millimoles) of powdered cobalt (II, III) oxide and 75 milligrams (0.219 millimoles) of dicobalt octacarbonyl. To this was added 17 ml of MTBE containing 1% weight water. The reactor was sealed, purged with nitrogen and placed under 1125 psi of 1:1 synthesis gas ($H_2$:CO). The sealed reactor was heated to 120° C. over the course of several minutes and the internal pressure was allowed to rise. The progress of the reaction was monitored quantitatively by changes in the infrared spectrum and by the consumption of syn gas. The formation of cobalt carbonyls was monitored by the growth of the metal carbonyl bands in the region from 2100 to 1960 $cm^{-1}$. The formation of cobalt carbonyls was accompanied by a rapid consumption of syn gas. Complete conversion of the cobalt oxides to cobalt carbonyls was observed within 70 minutes of reaching 120° C. When the reaction mixture was cooled and the liquid removed, an homogeneous, dark coffee brown solution characteristic of cobalt carbonyl mixtures was obtained. No precipitates of any kind were noted.

EXAMPLE 8

Cobalt Preforming with Cobalt Oxide

This experiment illustrates preforming of cobalt catalyst from cobalt carbonate in the presence of water and catalyst seed.

Into a 30-ml stainless steel autoclave fitted with internal infrared optics was added 660 milligrams (4.25 millimoles) of cobalt carbonate and 75 milligrams (0.219 millimoles) of dicobalt octacarbonyl. To this was added 17 ml of MTBE containing 1% weight water. The reactor was sealed, purged with nitrogen and placed under 1050 psi of 1:1 synthesis gas ($H_2$:CO). The sealed reactor was heated to 120° C. over the course of several minutes and the internal pressure was allowed to rise. The progress of the reaction was monitored quantitatively by changes in the infrared spectrum and by the consumption of syn gas. The formation of cobalt carbonyls was monitored by the growth of the metal carbonyl bands in the region from 2100 to 1960 $cm^{-1}$. The formation of cobalt carbonyls was accompanied by a rapid consumption of syn gas. Complete conversion of the cobalt carbonate to cobalt carbonyls was observed with 50 minutes of reaching 120° C. When the reaction mixture was cooled and the liquid removed, a homogeneous, dark, coffee brown solution characteristic of cobalt carbonyl mixtures was obtained. No precipitates of any kind were noted.

EXAMPLE 9

Effect of Water on Preforming

Into a 50-ml stainless steel autoclave fitted with internal infrared optics was added 450 milligrams (4.84 millimoles) of cobaltous hydroxide. To this was added 25 ml of anhydrous MTBE. The reactor was sealed, purged with nitrogen and placed under 1000 psi of 1:1 synthesis gas ($H_2$:CO). The sealed reactor was heated to 120° C. over the course of several minutes, the internal pressure was allowed to rise, and the temperature was allowed to stabilize. Using excess syn gas pressure, a solution of 40 milligrams of dicobalt octacarbonyl (0.117 millimoles) in 2 ml of dry MTBE was injected to the cobaltous hydroxide slurry. The progress of the conversion of cobaltous hydroxide was monitored quantitatively by changes in the infrared spectrum and consumption of syn gas. Complete conversion (>98%, as measured by absorbance intensities of the metal carbonyl region) was observed approximately 250 minutes following the introduction of cobalt carbonyl seed. When the reaction mixture was cooled and the liquid removed, a homogeneous, dark, coffee brown solution characteristic of cobalt carbonyl mixtures was obtained. No precipitates of any kind were noted.

The reaction was repeated using water-saturated MTBE instead of anhydrous MTBE. Complete conversion of cobalt hydroxide to cobalt carbonyls was achieved approximately 30 minutes after the introduction of the cobalt carbonyl seed. No precipitates of any kind were noted in the cooled reaction mixture.

We claim:

1. A process for preparing 1,3-propanediol comprising the steps of:

(a) reacting, in the presence of water and a seed compound, a precursor compound selected from at least one of cobalt hydroxide, cobalt (II,III) oxide and cobalt carbonate with synthesis gas in an essentially non-water-miscible liquid medium under conditions effective to produce a cobalt carbonyl reaction product mixture comprising at least one active cobalt carbonyl hydroformylation catalyst species;

(b) contacting ethylene oxide with synthesis gas in an essentially non-water-miscible liquid medium in the presence of a catalytic amount of the cobalt carbonyl reaction product mixture and an effective amount of a catalyst promoter under reaction conditions effective to produce an intermediate product mixture comprising less than 15 wt % 3-hydroxypropanal;

(c) adding an aqueous liquid to said intermediate product mixture and extracting into said aqueous liquid a major portion of the 3-hydroxypropanal so as to provide an aqueous phase comprising 3-hydroxypropanal in greater concentration than the concentration of 3-hydroxypropanal in the intermediate product mixture, and an organic phase comprising a major portion of the cobalt carbonyl;

(d) separating the aqueous phase from the organic phase;

(e) returning a major portion of the organic phase to the process of step (b);

(f) contacting the aqueous phase comprising 3-hydroxypropanal with hydrogen in the presence of a hydrogenation catalyst under hydrogenation conditions to provide a hydrogenation product mixture comprising 1,3-propanediol; and (g) recovering 1,3-propanediol from the hydrogenation product mixture.

2. The process of claim 1 in which the liquid medium of steps (a) and (b) is an ether.

3. The process of claim 1 in which the liquid medium of steps (a) and (b) is methyl-t-butyl ether.

4. The process of claim 1 in which step (a) is carried out at a temperature within the range of about 60° to about 140° C. and a pressure within the range of about 400 to about 2500 psig.

5. The process of claim 1 in which the water is present in step (a) in an amount within the range of about 0.5 wt % to about 3 wt %, based on the weight of the liquid medium.

6. The process of claim 1 in which the precursor compound of step (a) is cobalt hydroxide.

7. The process of claim 5 in which the seed compound is a cobalt carbonyl.

8. The process of claim 1 in which step (a) is carried out in a catalyst preparation vessel and step (b) is carried out in a separate hydroformylation vessel.

9. The process of claim 1 in which step (b) is carried out in a hydroformylation vessel and step (a) is carried out in situ in the hydroformylation vessel.

10. The process of claim 1 in which the seed compound is selected from the group consisting of nonylpyridine and cobalt octacarbonyl.

11. The process of claim 1 in which the precursor compound is a cobalt oxide.

12. The process of claim 1 in which the seed precursor compound is a cobalt carbonate.

13. A process for preparing 1,3-propanediol comprising the steps of:

(a) reacting cobalt hydroxide, in the presence of water and a seed compound, with synthesis gas in an essentially non-water-miscible liquid medium under conditions effective to produce a cobalt carbonyl reaction product mixture comprising at least one active cobalt carbonyl hydroformylation catalyst species;

(b) contacting ethylene oxide with synthesis gas in an essentially non-water-miscible liquid medium in the presence of a catalytic amount of the cobalt carbonyl reaction product mixture and an effective amount of a catalyst promoter under reaction conditions effective to produce an intermediate product mixture comprising less than 15 wt % 3-hydroxypropanal;

(c) adding water to said intermediate product mixture and extracting into said water a major portion of the 3-hydroxypropanal so as to provide an aqueous phase comprising 3-hydroxypropanal in greater concentration than the concentration of 3-hydroxypropanal in the intermediate product mixture, and an organic phase comprising a major portion of the cobalt carbonyl;

(d) separating the aqueous phase from the organic phase;

(e) returning a major portion of the organic phase to the process of step (b);

(f) contacting the aqueous phase comprising 3-hydroxypropanal with hydrogen in the presence of a hydrogenation catalyst under hydrogenation conditions to provide a hydrogenation product mixture comprising 1,3-propanediol; and (g) recovering 1,3-propanediol from the hydrogenation product mixture.

\* \* \* \* \*